United States Patent [19]

Applebaum

[11] Patent Number: 5,306,299
[45] Date of Patent: Apr. 26, 1994

[54] MIDDLE EAR PROSTHESIS

[75] Inventor: Edward Applebaum, Chicago, Ill.

[73] Assignee: Smith & Nephew Richards, Inc., Memphis, Tenn.

[21] Appl. No.: 948,121

[22] Filed: Sep. 21, 1992

[51] Int. Cl.⁵ .............................................. A61F 2/18
[52] U.S. Cl. .................................................... 623/10
[58] Field of Search ....................... 623/10, 11, 12, 16; 606/61, 73, 75, 60

[56] References Cited

U.S. PATENT DOCUMENTS

| | | | |
|---|---|---|---|
| 3,196,462 | 7/1965 | Robinson | 623/10 |
| 4,655,776 | 4/1987 | Lesinski | 623/10 |
| 5,147,402 | 9/1992 | Bohler et al. | 606/61 |
| 5,163,957 | 11/1992 | Sadé et al. | 623/10 |
| 5,176,678 | 1/1993 | Tsou | 606/61 |

OTHER PUBLICATIONS

*Atlas of Otologic Surgery*, W. B. Saunders Company, pp. 63–65 (1989).
B. W. Armstrong, et al., "Experiences With the Ossicular Chain," Reprinted from 78 *Annals of Otology, Rhinology and Laryngology*, 5, p. 939 (1969).

Primary Examiner—David Isabella
Attorney, Agent, or Firm—Pravel, Hewitt, Kimball & Krieger

[57] ABSTRACT

Disclosed is a prosthetic device for replacing a portion of the incus when the stapes or a portion of the lenticular process is generally intact. The device comprises an opening for receiving the head of the stapes or a portion of the lenticular process and a channel for receiving the remnant portion of the incus. The opening and the channel are oriented to allow proper functioning of the ossicular chain.

9 Claims, 2 Drawing Sheets

MIDDLE EAR PROSTHESIS

BACKGROUND OF THE INVENTION

1. Field of the Invention

This invention relates to a prosthetic device that is used in the surgical reconstruction of a portion of the small bones that form the ossicular chain in the middle ear. More specifically, a prosthesis has been developed for partially rebuilding the incus when either all or part of the long process or lenticular process of the incus has eroded.

2. Description of the Related Art

Sound waves enter the outer ear canal and cause the tympanic membrane to vibrate at a rate which corresponds to the frequency of the sound waves. The vibrations are transmitted to the middle ear through a series of three tiny bones that form what is called the ossicular chain. These bones are the malleus, incus and the stapes. They operate to transport the vibrations from the tympanic membrane to the cochlea, enabling the hearer to perceive sound.

These bones are connected so the vibrations can be transmitted along the entire chain. The three bones are connected in series through joints that allow the bones to move relative to each other and transmit vibrations through a highly efficient lever action. The malleus is vibrated through its connection with the tympanic membrane. The malleus is connected through the incudo-malleolar joint to the incus, which enables vibrations to be imparted to the incus, through the incudo-stapedial joint and then to the stapes. The incudo-malleolar joint is significant in the faithful transmission of vibrations through the ossicular chain because of the relatively large contact area between the malleus and incus.

One of the most common maladies in the ossicular chain results from a lesion caused by chronic otitis media. This lesion can form on the lenticular process of the incus and causes the lenticular process and the connection between the incus and stapes to deteriorate. However, it can also form along the long process, leaving the incudo-stapedial joint intact.

Medical implants have been developed to reconstruct the ossicular chain when a portion of the incus is missing. However, all of the known implants involve complete replacement of the incus, which destroys the natural joint between the malleus and the incus as well as the joint between the incus and stapes. The resulting structure is less efficient than the natural joints because the implant replaces them with rigid connections.

Techniques have also been developed which use autograph cartilage from the host's body as a wedge between the remnant incus and stapes in order to reconstruct the ossicular chain. This technique also affects the natural action of the incudo-malleolar joint because the wedge is connected to the malleus and incus as well as the stapes. A combined medical prosthesis and magnet is suggested in U.S. Pat. No. 4,606,329 to Hough, which is implanted, among other places, between the incus and stapes. However, the device bypasses the normal vibratory function of the bones in the ossicular chain and imparts vibrations directly to the stapes.

In current practice, when the lenticular process of the incus has eroded, but the stapes and the main incus body are generally intact, the incus is surgically removed and entirely replaced with an implant. This practice requires the incudo-malleolar joint to be replaced with a rigid connection that does not effectively transmit the vibratory motion. It would a better practice to utilize the remaining natural bone of the incus without replacing it entirely with a prosthesis, thus leaving the incudo-malleolar joint intact.

Therefore, there is a clinical need for a prosthesis that allows reconstruction of a portion of the incus without complete replacement and connects to either the generally healthy stapes or the healthy portion of the lenticular process for maintaining most of the natural action of the ossicular chain.

SUMMARY OF THE INVENTION

The invention is directed to a middle ear prosthesis that replaces a diseased portion of the incus and provides a connection between the remaining portions of the incus or the incus and the stapes without requiring complete replacement of the incus. By replacing only a portion of the incus, the natural lever action between the malleus and the incus remains intact resulting in more effective transmission of vibrations through the ossicular chain. When the incudo-stapedial joint is replaced, although a rigid joint is formed between the stapes and the incus, this does not significantly effect the transmission of vibrations to the cochlea.

The prosthesis is fabricated from synthetic biomaterials, preferably a calcium phosphate ceramic such as hydroxyapatite. Sound waves travel through hydroxyapatite in a manner similar to their transmission through bone. Hydroxyapatite also avoids the complications associated with human bone grafts and allows the prosthesis to be stored in a sterile condition, ready for use.

The prosthesis has a generally L-shaped or elbow shaped body with a first leg having a U-shaped or open channel for receiving a remnant portion of the incus. The channel is open along the outer side of the first leg so that it can receive varying lengths of such a remnant portion. A circular opening is formed in the other leg, intersecting the channel, for receiving either the head of the generally intact stapes or a portion of the lenticular process when it can be used.

In order to implant the prosthesis, the head of the stapes or the medial end of the lenticular process is placed into the circular opening. Afterward the remnant portion of the incus is laid into the U-shaped channel. Compression between the malleus, incus and stapes holds the prosthesis in place. After a period of time the prosthesis becomes an integral part of the incus and stapes due to growth of bone tissue around the uneven hydroxyapatite surface.

DETAILED DESCRIPTION OF THE PREFERRED EMBODIMENT

The present invention is directed to a prosthetic device that is used for partially rebuilding the incus when a portion of the long process or its lenticular process has eroded, and the stapes is generally intact.

Figure 1:
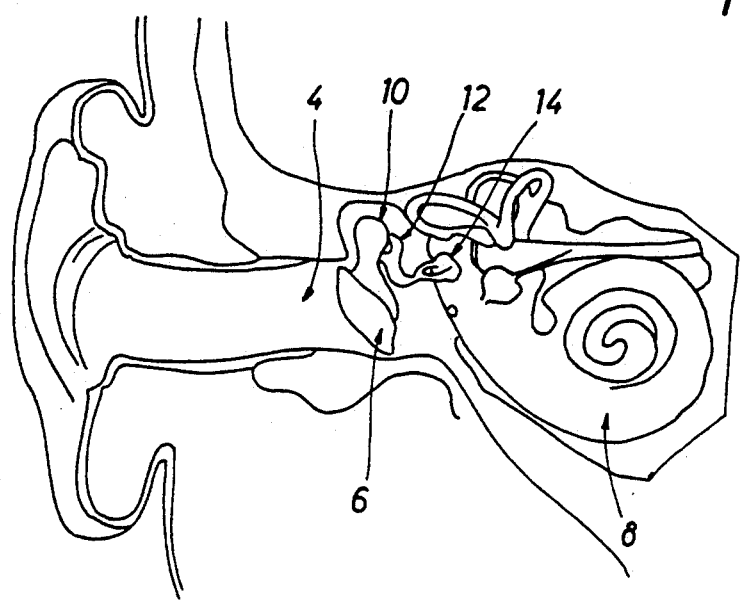
FIG. 1 is a cross-sectional view of a human ear.
Figure 2:
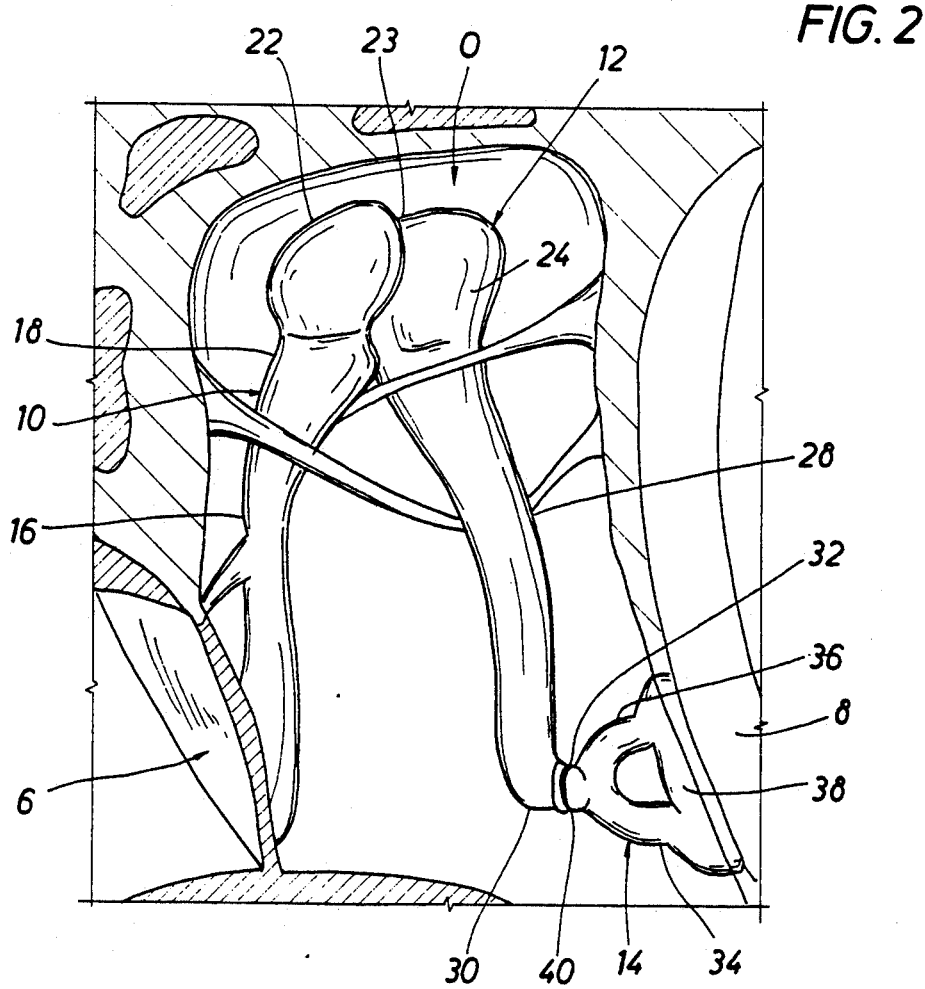
FIG. 2 is a perspective view of the bones that form the ossicular chain.

FIG. 1 shows the elements of a human ear and FIG. 2 is an enlarged view of a cavity known as the middle ear. Sound waves travel down the ear canal 4 and cause the tympanic membrane 6 to vibrate. The vibrations are transmitted to the middle ear by a sequence of three tiny bones that form the ossicular chain, the malleus 10, the incus 12 and the stapes 14. The stapes 14 contacts a membrane-covered opening in the bony wall of the cochlea 8 and transmits the vibrations to fluids inside the cochlea 8. The vibrations create waves on a membrane running along the length of the cochlea 8 and nerve impulses from the membrane are relayed to the brain where they are transmitted into sound.

The incus 12 has a body portion 24 which is connected to the malleus 10 through an incudo-malleolar joint 23. The incus 12 also has a long process 28 and a lenticular process 30, the latter being connected to a head 32 of the stapes 14 at an incudo-stapedial joint 40.

Figure 3:
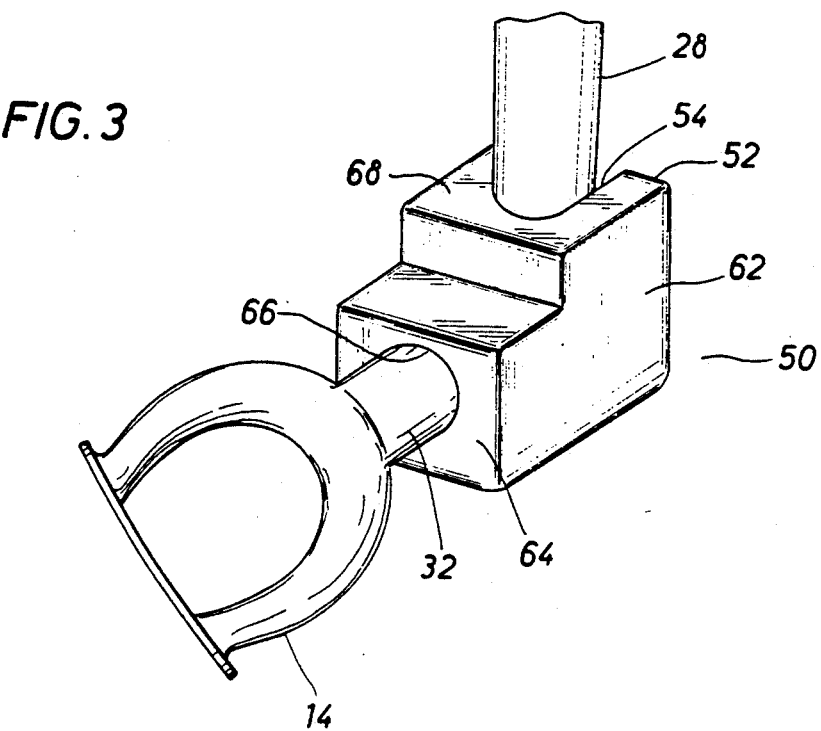
FIG. 3 is a perspective view of a prosthesis of the present invention implanted between the stapes and incus.
Figure 4:
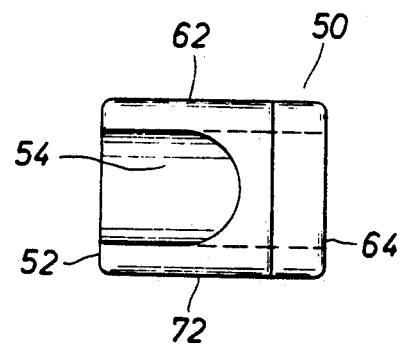
FIG. 4 is a top view of the prosthesis of FIG. 3, with dotted lines illustrating the opening in which the end of the stapes is inserted.
Figure 5:
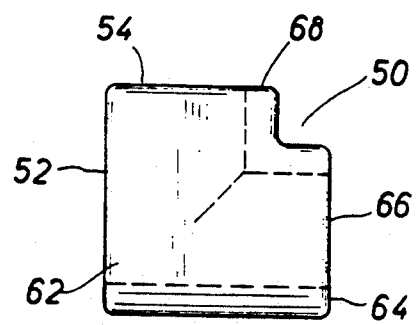
FIG. 5 is a side view of the prosthesis of FIG. 3 with dotted lines showing the internal openings for receiving the adjacent portions of the incus and lenticular process or stapes.

FIG. 3 shows a prosthesis 50 of the present invention with the head 32 of the stapes 14 and long process 28 of the incus 12 implanted. While prosthesis 50 may be of any suitable shape, in the embodiment shown it is a generally L-shaped or elbow-shaped body. One leg 52 of the prosthesis 50 has a U-shaped or open channel 54 which extends along the outer side of the leg 52, as shown best in FIGS. 4–6. A second leg 64 of the prosthesis 50 has a circular opening 66 in the approximate center of the surface of leg 64. The axis of the U-shaped channel 54 is generally perpendicular to the axis of the circular opening 66. The U-shaped channel 54 and the circular opening 66 intersect creating a continuous interior chamber. The channel 54 terminates at the opening 66. In a preferred embodiment, the leg 52 is about 0.098 to 0.078 in. long. The other leg 64 is about 0.059 in. long. The channel 54 is about 0.039 in. deep, and the inside diameter of the circular opening 66 is about 0.039 in. The side 62 of the prosthesis 50 is about 0.078 in. long. The width of the prosthesis 50 from the side 62 to the side 72 is about 0.059 in.

The prosthesis 50 is preferably fabricated from a calcium phosphate ceramic such as hydroxyapatite (HA), although other biocompatible materials can be used. HA has a crystal structure which resists biodeterioration and has a rough outer surface to which new tissue, generated by the adjacent body part, can easily adhere. After a period of time the implanted prosthesis 50 becomes an integral part of the incus 12 and stapes 14 due to growth of the bone tissue and its adherence to the hydroxyapatite material. To facilitate the insertion of the prosthesis 50 and to protect the delicate middle ear membranes all edges of the prosthesis 50 are rounded off.

In its preferred embodiment, the prosthesis 50 is fabricated in at least two sizes. One size has a leg 52 formed about 0.078 in. long, and in a second preferred embodiment a leg 52 about 0.098 in. long. These sizes should be able to accommodate most incus defects. The other dimensions of the prosthesis 50 remain the same for both sizes.

Figure 6:
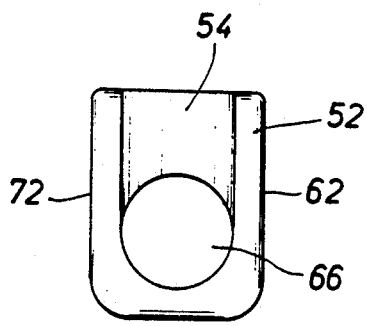
FIG. 6 is an end view of the prosthesis of FIG. 3.

As shown in FIG. 3, the lenticular process 30 and a small portion of the long process 28 of the incus 12 have eroded, and the prosthesis 50 is used to replace the incudo-stapedial joint 40 and bridge the gap between the remanent incus body 12 and the stapes 14. The prosthesis 50 is preferably implanted by first inserting the head 32 of the stapes 14 into the circular opening 66. Proper positioning of the prosthesis 50 is determined by observing the head 32 of the stapes 14 through the intersecting space between the circular opening 66 and the U-shaped channel 54 as shown in FIG. 6. Centering the head 32 of the stapes 14 into the circular opening 66 assures proper positioning of the prosthesis 50.

The remnant long process 28 of the incus 12 is then positioned into the U-shaped channel 54. The length of the long process 28 that is inserted into the U-shaped channel 54 varies depending upon the length of the remnant incus 12.

After the head 32 of the stapes 14 is inserted into the circular opening 66, and the long process 28 of the incus 12 is inserted into the U-shaped channel 54, natural compression that occurs between the malleus 10, the incus 12 and the stapes 14 holds the prosthesis 50 in place. Proper positioning is determined by carefully palpating the malleus 10 to verify good motion transmission through the prosthesis 50 to the stapes 14.

In an alternative use the prosthesis 50 can be used when the incudo-stapedial joint 40 and a portion of the lenticular process 30 is intact, but a section of the long process 28 is diseased. In this alternative use the prosthesis 50 is preferably implanted by first inserting the medial end of the intact portion of the lenticular process 30 into the circular opening 66. Proper positing of the prosthesis 50 is determined by observing the section of the intact lenticular process 30 through the intersecting space between the circular opening 66 and the U-shaped channel 54, as shown in FIG. 6.

The remnant long process 29 of the incus 12 is then positioned into the U-shaped channel 54. The length of the long process 28 that is inserted into the U-shaped channel 54 varies depending upon the length of the remnant incus 12.

Natural compression that occurs between the malleus 10, the incus 12 and the stapes 14 holds the prosthesis 50 in place. Proper positioning is determined by carefully palpating the malleus 10 to verify good motion transmission through the prosthesis 50 to the stapes 14.

As a result of natural tissue growth, the prosthesis 50 eventually becomes an integral part of the incus 12 or the incus 12 and stapes 14 with bone tissue adhering to the outer surface of the HA body. By replacing only a portion of the incus 12, the natural connection between the malleus 10 and the incus 12 is preserved. The foregoing is illustrative of the present invention, but not limiting. Numerous variations and modifications can be effective without departing from the true scope and spirit of the invention.

I claim:

1. A prosthesis for connecting a remnant portion of an incus with either a portion of the lenticular process of the incus or a substantially intact stapes, comprising;
   a body formed of a biocompatible material defining
   (a) an elongated opening having an axis of symmetry adapted to receive the lenticular process of the incus or a head of the stapes; and (b) an elongated channel open along one side of the body and having a plane of symmetry adapted to receive a remnant portion of the long process of the incus;
   wherein the opening and channel intersect and are oriented such that the axis of symmetry of the opening is oriented normal to a plane generally perpendicular to the plane of symmetry of the channel; and the body being sized and shaped to provide a connection between the remnant portion of the incus and one of the portion of the lenticular process of the incus or the substantially intact stapes.

2. The prosthesis of claim 1, wherein the prosthesis is formed from a calcium phosphate ceramic such as hydroxyapatite.

3. The prosthesis of claim 1, wherein the channel is U-shaped.

4. The prosthesis of claim 1, wherein the body comprises two legs oriented generally perpendicular to each other, with the channel and the opening each positioned in a leg.

5. A prosthesis for connecting a remnant portion of the long process of an incus with a substantially intact stapes or portion of a lenticular process, comprising;

a body defining (a) an elongated opening adapted to receive a head of the stapes or portion of the lenticular process; and (b) an elongated channel open along one side of the body adapted to receive a long process of the incus;

wherein the opening and channel intersect and are oriented to maintain the incus and the stapes generally in their natural orientation; and the body being sized and shaped to provide a connection between the long process of the incus and one of the portion of the lenticular process of the incus or the substantially intact stapes.

6. The prosthesis of claim 5, wherein the prosthesis is formed from a calcium phosphate ceramic such as hydroxyapatite.

7. The prosthesis of claim 5, wherein the channel is U-shaped.

8. The prosthesis of claim 5, wherein the body comprises two legs oriented generally perpendicular to each other with the channel and the opening each positioned in a leg.

9. A method for connecting a remnant portion of an incus with a substantially intact stapes or portion of a lenticular process comprising;

providing a prosthesis body which includes a first elongated opening and a second elongated channel open at one end;

inserting the head of the stapes or portion of the lenticular process into the first elongated opening;

centering the head of the stapes or portion of the lenticular process in the first elongated opening by observing the stapes head or lenticular process portion through an intersecting space between the first elongated opening and the second elongated channel;

positioning a remnant portion of the incus into the second elongated channel; and palpating the malleus to verify sufficient motion transmission through the prosthesis to the stapes.

* * * * *